(12) United States Patent
Linker et al.

(10) Patent No.: US 6,350,720 B2
(45) Date of Patent: *Feb. 26, 2002

(54) SUBSTITUTED PHENYLTRIAZOLIN(THI)ONES AND THEIR USE AS HERBICIDES

(75) Inventors: Karl-Heinz Linker, Leverkusen; Wilhelm Haas, Pulheim; Otto Schallner, Monheim, all of (DE); Markus Dollinger, Overland Park, KS (US)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/341,802
(22) PCT Filed: Jan. 14, 1998
(86) PCT No.: PCT/EP98/00177
    § 371 Date: Jul. 19, 1999
    § 102(e) Date: Jul. 19, 1999
(87) PCT Pub. No.: WO98/32746
    PCT Pub. Date: Jul. 30, 1998

(30) Foreign Application Priority Data

Jan. 27, 1997 (DE) .......................... 197 02 786

(51) Int. Cl.[7] ...................... A01N 43/653; C07D 249/08
(52) U.S. Cl. ................. 504/273; 548/263.2; 548/263.4; 548/263.8; 548/264.4
(58) Field of Search ...................... 504/273; 548/263.2, 548/263.4, 263.8, 264.4

(56) References Cited

U.S. PATENT DOCUMENTS

| | | | |
|---|---|---|---|
| 5,464,810 A | 11/1995 | Haas et al. | 504/273 |
| 5,593,945 A | 1/1997 | Andree et al. | 504/243 |
| 5,663,362 A | 9/1997 | Haas et al. | 548/263.2 |

FOREIGN PATENT DOCUMENTS

WO 96/35679 11/1996

OTHER PUBLICATIONS

Cram and Hammond, "Organic Chemistry", McGraw Hill Book Co., NY, (1964) 2nd Ed. pp 565–567.*

* cited by examiner

Primary Examiner—Patricia L. Morris
(74) Attorney, Agent, or Firm—Joseph C. Gil

(57) ABSTRACT

The invention relates to new substituted phenyltriazolin(thi)one of the general formula (I),

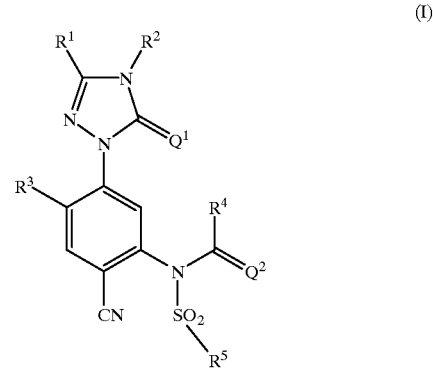

in which $Q^1$, $Q^2$, $R^1$, $R^2$, $R^3$, $R^4$ and $R^5$ have the meanings given in the description, and to a process for their preparation and to their use as herbicides.

6 Claims, No Drawings

SUBSTITUTED PHENYLTRIAZOLIN(THI)ONES AND THEIR USE AS HERBICIDES

The invention relates to new substituted phenyltriazolin(ethi)ones, to processes for their preparation and to their use as herbicides.

It has already been disclosed that certain substituted phenyltriazolin(ethi)ones have herbicidal properties (cf. EP 609734/U.S. Pat. No. 5,464,810). However, the substituted phenyltriazolin(ethi)ones which have been disclosed have not gained any particular significance.

There have now been found new substituted phenyltriazolin(ethi)ones of the general formula (I)

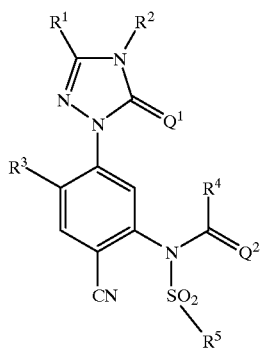

(I)

in which $Q^1$ and $Q^2$ are identical or different and represent O or S, $R^1$ represents hydrogen, cyano, halogen or one of the radicals —$R^6$, —O—$R^6$, —S$R^6$, —SO—$R^6$ or —SO$_2$—$R^6$, $R^2$ represents hydrogen, hydroxyl, amino or one of the radicals —$R^6$, —O—$R^6$ or —N=C$R^6R^7$, $R^3$ represents hydrogen, halogen, alkyl or halogenoalkyl, $R^4$ represents hydrogen, alkoxycarbonyl or one of the radicals —$R^6$, —O—$R^6$, —S$R^6$, —NH—$R^6$ or —N$R^6R^7$, $R^5$ represents amino, hydroxyl or one of the radicals —$R^6$ or —N$R^6R^7$, $R^6$ represents a radical from amongst alkyl, alkenyl, alkinyl, cycloalkyl, aryl, arylalkyl, aryloxyalkyl, arylalkoxyalkyl, heterocyclyl or heterocyclylalkyl, each of which is optionally substituted, and $R^7$ represents hydrogen or a radical from amongst alkyl, alkenyl, alkinyl or cycloalkyl, each of which is optionally substituted.

Furthermore, it has been found that the new substituted phenyltriazolin(ethi)ones of the general formula (I) are obtained when phenyltriazolin(ethi)ones of the general formula (II)

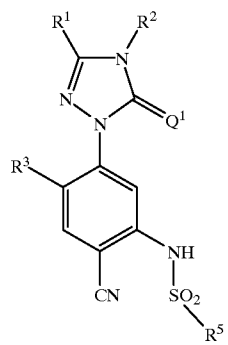

(II)

in which $Q^1$, $R^1$, $R^2$, $R^3$ and $R^5$ have the abovementioned meanings, are reacted with halogeno(thio)carbonyl compounds of the general formula (III)

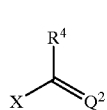

(III)

in which $Q^2$ and $R^4$ have the abovementioned meanings and

X represents halogen, if appropriate in the presence of a reaction auxiliary and if appropriate in the presence of a diluent.

Furthermore, it has been found that the new substituted phenyltriazolin(ethi)ones of the general formula (I) are distinguished by a potent and selective herbicidal activity. Formula (I) provides a general definition of the substituted phenyltriazolin(ethi)ones according to the invention. Preferred compounds of the formula (I) are those in which $Q^1$ and $Q^2$ are identical or different and represent O or S, $R^1$ represents hydrogen, cyano, fluorine, chlorine, bromine, iodine or one of the radicals —$R^6$, —O—$R^6$, —S—$R^6$, —SO—$R^6$ or —SO$_2$—$R^6$, $R^2$ represents hydrogen, hydroxyl, amino or one of the radicals —$R^6$, —O—$R^6$ or —N=C$R^6R^7$, $R^3$ represents hydrogen, fluorine, chlorine, bromine, iodine, or represents straight-chain or branched alkyl having 1 to 4 carbon atoms or straight-chain or branched halogenoalkyl having 1 to 4 carbon atoms and 1 to 3 identical or different halogen atoms—in particular fluorine, chlorine or bromine, $R^4$ represents hydrogen, alkoxycarbonyl having 1 to 6 carbon atoms in the alkoxy group, or one of the radicals —$R^6$, —O—$R^6$, —S—$R^6$, —NH—$R^6$ or —N$R^6R^7$, $R^5$ represents amino, hydroxyl or one of the radicals —$R^6$ or —N$R^6R^7$, $R^6$ represents straight-chain or branched alkyl having 1 to 10 carbon atoms which is optionally monosubstituted or polysubstituted by identical or different substituents, preferred substituents being:

halogen—in particular fluorine, chlorine and/or bromine, cyano, carboxyl, carbamoyl, thiocarbamoyl, in each case straight-chain or branched alkoxy, alkoxyalkoxy, alkylthio, alkylsulphinyl, alkylsulphonyl, alkoxycarbonyl, N-alkyl-amninocarbonyl, N,N-dialkyl-aminocarbonyl, trialkylsilyl or alkylsulphonylaminocarbonyl, each of which has 1 to 6 carbon atoms in the individual alkyl moieties, or heterocyclyl, the heterocyclyl radical being a five- to seven-membered saturated or unsaturated heterocycle which has 1 to 3 identical or different hetero atoms—in particular nitrogen, oxygen and/or sulphur—and which is optionally benzo-fused;

$R^6$ furthermore represents alkenyl or alkini, each of which has 2 to 8 carbon atoms and each of which is optionally monosubstituted or polysubstituted by identical or different halogen substituents—in particular fluorine, chlorine and/or bromine;

$R^6$ furthermore represents cycloalkyl having 3 to 7 carbon atoms which is optionally monosubstituted or polysubstituted by identical or different halogen substituents—in particular fluorine, chlorine and/or bromine—and/or straight-chain or branched alkyl having 1 to 4 carbon atoms;

$R^6$ furthermore represents aryl, arylalkyl, aryloxyalkyl or arylalkoxyalkyl, each of which has 6 to 10 carbon atoms in the aryl moiety and, if appropriate, 1 to 4 carbon atoms in the straight-chain or branched alkyl moiety and each of which is optionally monosubstituted or polysubstituted in the aryl moiety by identical or different substituents, or represents a saturated or unsaturated, five- to seven-membered heterocyclyl radical which has 1 to 3 identical or different hetero atoms—in particular nitrogen, oxygen and/or sulphur—and which is optionally monosubstituted or polysubstituted by identical or different substituents and/or benzo-fused, preferred aryl or heterocyclyl substituents being:

halogen, cyano, nitro, amino, N-acetyl-amino, in each case straight-chain or branched alkyl, alkoxy, alkylthio, alkylsulphinyl or alkylsulphonyl, each of which has 1 to 6 carbon atoms, in each case straight-chain or branched halogenoalkyl, halogenoalkoxy, halogeroalkylthio, halogenoalkylsulphinyl or halogenoalkylsulphonyl, each of which has 1 to 6 carbon atoms and 1 to 3 identical or different halogen atoms, in each case straight-chain or branched alkoxycarbonyl or alkoximinoalkyl, each of which has 1 to 6 carbon atoms in the individual alkyl moieties, and phenyl which is optionally monosubstituted or polysubstituted by identical or different substituents from amongst halogen and/or straight-chain or branched alkyl or alkoxy, each of which has 1 to 6 carbon atoms, and/or straight-chain or branched halogenoalkyl or halogenoalkoxy, each of which has 1 to 6 carbon atoms and 1 to 3 identical or different halogen atoms;

$R^7$ represents hydrogen, or represents alky having 1 to 8 carbon atoms which is optionally monosubstituted or polysubstituted by identical or different substituents, suitable substituents being:

halogen—in particular fluorine, chlorine and/or bromine, cyano, carboxyl, carbamoyl, thiocarbamoyl, in each case straight-chain or branched alkoxy, alkoxyalkoxy, alkylthio, alkylsulphinyl, alkylsulphonyl, alkoxycarbonyl, N-alkyl-aminocarbonyl, N,N-dialkyl-aminocarbonyl, trialkylsilyl or alkylsulphonylaminocarbonyl, each of which has 1 to 8 carbon atoms in the individual alkyl moieties, or heterocyclyl, and the heterocyclyl being a five- to seven-membered saturated or unsaturated heterocycle which has 1 to 3 identical or different hetero atoms—in particular nitrogen, oxygen and/or sulphur—and which is optionally benzo-fused;

$R^7$ furthermore represents alkenyl or alkinyl, each of which has 2 to 8 carbon atoms and each of which is optionally monosubstituted or polysubstituted by identical or different halogen substituents—in particular fluorine, chlorine and/or bromine;

$R^7$ furthermore represents cvcloalkyl having 3 to 7 carbon atoms which is optionally monosubstituted or polysubstituted by identical or different substituents from amongst halogen—in particular fluorine, chlorine and/or bromine—and/or straight-chain or branched alkyl having 1 to 4 carbon atoms.

Especially preferred compounds of the formula (I) are those in which $Q^1$ and $Q^2$ are identical or different and represent O or S, $R^1$ represents hydrogen, fluorine, chlorine, bromine or one of the radicals —$R^6$, —O—$R^6$, —S$R^6$, —SO—$R^6$ or —SO$_2$—$R^6$, $R^2$ represents hydrogen, hydroxyl, amino or one of the radicals —$R^6$, —O—$R^6$ or —N=C$R^6R^7$, $R^3$ represents hydrogen, fluorine, chlorine, bromine, straight-chain or branched alkyl having 1 to 3 carbon atoms or straisght-chain or branched halogenoalkyl having 1 to 3 carbon atoms and 1 to 3 identical or different halogen atoms—in particular fluorine or chlorine, $R^4$ represents hydrogen, alkoxycarbonyl having 1 to 4 carbon atoms in the alkoxy group, or one of the radicals —$R^6$, —O—$R^6$, —S—$R^6$, —NH—$R^6$ or —N$R^6R^7$, $R^5$ represents amino, hydroxyl or one of the radicals —$R^6$ or —N$R^6R^7$, $R^6$ represents straight-chain or branched alkiy having 1 to 6 carbon atoms which is optionally monosubstituted, preferred substituents being:

cyano, carboxyl, carbamoyl, thiocarbamoyl, in each case straight-chain or branched alkoxy, alkoxyalkoxy, alkylthio, alkylsulphinyl, alkylsulphonyl, alkoxycarbonyl, N-alkyl-aminocarbonyl, N,N-dialkyl-aminocarbonyl, trialkylsilyl or alkylsulphonylaminocarbonyl, each of which has 1 to 4 carbon atoms in the individual alkyl moieties, or heterocyclyl, the heterocyclyl radical being a five- or six-membered saturated or unsaturated heterocycle having 1 to 3 identical or different hetero atoms—in particular nitrogen, oxygen and/or sulphur;

$R^6$ furthermore represents straight-chain or branched halogenoalkyl having 1 to 4 carbon atoms and 1 to 3 identical or different halogen atoms—in particular fluorine, chlorine or bromine;

$R^6$ furthermore represents alkenyl or alkinyl, each of which has 2 to 6 carbon atoms and each of which is optionally monosubstituted to trisubstituted by identical or different halogen substituents—in particular fluorine, chlorine or bromine;

$R^6$ furthermore represents cycloalkyl having 3 to 6 carbon atoms which is optionally monosubstituted to trisubstituted by identical or different substituents from amongst halogen—in particular fluorine, chlorine or bromine—and/or straight-chain or branched alkyl having 1 to 3 carbon atoms;

$R^6$ furthermore represents phenyl, phenylalkyl or phenoxyalkyl, each of which is optionally monosubstituted to trisubstituted in the phenyl moiety by identical or different substituents and, if appropriate, has 1 to 3 carbon atoms in the straight-chain or branched alkyl moiety, or represents a saturated or unsaturated, five- to six-membered heterocyclyl radical having 1 to 3 identical or different hetero atoms—in particular nitrogen, oxygen and/or sulphur—and which is optionally monosubstituted to trisubstituted by identical or different substituents and/or benzo-fused, especially preferred phenyl or heterocyclyl substituents being:

fluorine, chlorine, bromine, cyano, nitro, amino, N-acetyl-amino, in each case straight-chain or branched alkyl, alkoxy, alkylthio, alkylsulphinyl or alkylsulphonyl, each of which has 1 to 4 carbon atoms, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 3 identical or different halogen atoms (in particular fluorine or chlorine), in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents from amongst halogen and/or straight-chain or branched alkyl or alkoxy, each of which has 1 to 4 carbon atoms, and/or straight-chain or branched halogenoalkyl or halogenoalkoxy, each of which has 1 to 4 carbon atoms and 1 to 3 identical or different halogen atoms;

$R^7$ represents hydrogen or straight-chain or b3alkyl having 1 to 4 carbon atoms which is optionally monosubstituted, especially preferred substituents being:

cyano, carboxyl, carbamoyl, in each case straight-chain or branched alkoxy, alkoxyalkoxy, alkylthio, alkylsulphinyl, alkylsulphonyl, alkoxycarbonyl, N-alkyl-aminocarbonyl, N,N-dialkyl-aminocarbonyl, trialkylsilyl or alkylsulphonylaminocarbonyl, each of which has 1 to 4 carbon atoms in the individual alkyl moieties, or heterocyclyl, the heterocyclyl radical being a five- or six-membered, saturated or unsaturated heterocycle having 1 to 3 identical or different hetero atoms—in particular nitrogen, oxygen and/or sulphur;

$R^7$ furthermore represents straight-chain or branched halogenoalkyl having 1 to 4 carbon atoms and 1 to 3 identical or different halogen atoms—in particular fluorine or chlorine;

$R^7$ furthermore represents alkenyl or alkinyl, each of which has 2 to 4 carbon atoms and each of which is optionally monosubstituted to trisubstituted by identical or different halogen substituents—in particular fluorine, chlorine or bromine;

$R^7$ furthermore represents cycloalkyl having 3 to 6 carbon atoms which is optionally monosubstituted to trisubstituted by identical or different substituents from amongst halogen—in particular fluorine or chlorine—and/or straight-chain or branched alkyl having 1 to 3 carbon atoms.

Very especially preferred compounds of the formula (I) are those in which $Q^1$ and $Q^2$ are each O, $R^1$ represents hydrogen, chlorine, bromine or one of the radicals —$R^6$, —O—$R^6$, —S—$R^6$, —SO—$R^6$ or —$SO_2$—$R^6$, $R^2$ represents hydrogen or one of the radicals —$R^6$ or —O—$R^6$, $R^3$ represents hydrogen, fluorine or chlorine., $R^4$ represents hydrogen or one of the radicals —$R^6$, —O—$R^6$, —S—$R^6$, —NH—$R^6$ or —$NR^6R^7$, $R^5$ represents one of the radicals —$R^6$ or —$NR^6R^7$, $R^6$ represents methyl, ethyl, n- or i-propyl, n-, i-, s- or t-butyl, each of which is optionally monosubstituted or disubstituted, suitable substituents being:

cyano, carboxyl, carbamoyl, in each case straight-chain or branched alkoxy, alkoxyalkoxy, alkylthio, alkylsulphinyl, alkylsulphonyl, alkoxycarbonyl, N-alkyl-aminocarbonyl, N,N-dialkyl-aminocarbonyl, trialkylsilyl or alkylsulphonylaminocarbonyl, each of which has 1 to 4 carbon atoms in the individual alkyl moieties;

$R^6$ furthermore represents halogenoalkyl having 1 or 2 carbon atoms and 1 to 3 identical or different halogen atoms—in particular fluorine or chlorine;

$R^6$ furthermore represents alkenyl or alkinyl, each of which has 2 to 5 carbon atoms and each of which is optionally monosubstituted or disubstituted by halogen—in particular fluorine or chlorine;

$R^6$ furthermore represents cyclopropyl, cyclopentyl or cyclohexyl, each of which is optionally monosubstituted or disubstituted by identical or different substituents from amongst fluorine, chlorine, methyl and/or ethyl, $R^6$ furthermore represents phenyl, benzyl, furyl, thienyl or isoxazolyl, each of which is optionally monosubstituted, disubstituted or trisubstituted by identical or different substituents, especially preferred substituents in each case being:

fluorine, chlorine, bromine, cyano, nitro, amino, N-acetyl-amino, methyl, ethyl, n- or i-propyl, n-, i-, s- or t-butyl, imethoxy, ethoxy, n- or i-propoxy, n-, i-, s- or t-butoxy, methylthio, ethylthio, methylsulphinyl, methylsulphonyl, trifluoromethyl, difluoromethyl, trifluoromethoxy, difluoromethoxy, trifluoromethylthio, trifluoromethylsulphinyl, trifluoromethylsulphonyl, methoxycarbonyl, ethoxycarbonyl, methoximinomethyl, methoximinoethyl, ethoximinomethyl, ethoximinoethyl, $R^7$ represents hydrogen, or represents methyl, ethyl, n- or i-propyl, n- or i-butyl, each of which is optionally monosubstituted, suitable substituents being:

cyano, carboxyl, carbamoyl, in each case straight-chain or branched alkoxy, alkoxyalkoxy, alkylthio, alkylsulphinyl, alkylsulphonyl, alkoxycarbonyl, N-alkyl-aminocarbonyl, N,N-dialkyl-arminocarbonyl, each of which has 1 to 4 carbon atoms in the alkyl groups;

$R^7$ furthermore represents halogenoalkyl having 1 or 2 carbon atoms and 1 to 3 identical or different halogen atoms—in particular fluorine or chlorine;

$R^7$ furthermore represents alkenyl or alkinyl, each of which has 2 to 5 carbon atoms and each of which is optionally monosubstituted or disubstituted by halogen—in particular fluorine or chlorine, or $R^7$ furthermore represents cyclopropyl, cyclopentyl or cyclohexyl, optionally monosubstituted or disubstituted by identical or different substituents from amongst fluorine, chlorine, methyl and/or ethyl.

The definitions of radicals which have been given above, either in general or in preferred ranges, apply to the end products of the formula (I) and, analogously, to the starting materials or intermediates required in each case for the preparation. These definitions of radicals can be combined with each other as desired, that is to say combinations between the ranges given as preferred are also possible.

If, for example, 2-(2-chloro-4-cyano-5-ethylsulphonylamino-phenyl)-5-chloro-4-methyl-2,4-dihydro-3H-1,2,4-triazol-3-one and pivaloyl chloride are used as starting materials, the course of the reaction in the process according to the invention can be outlined by the following equation:

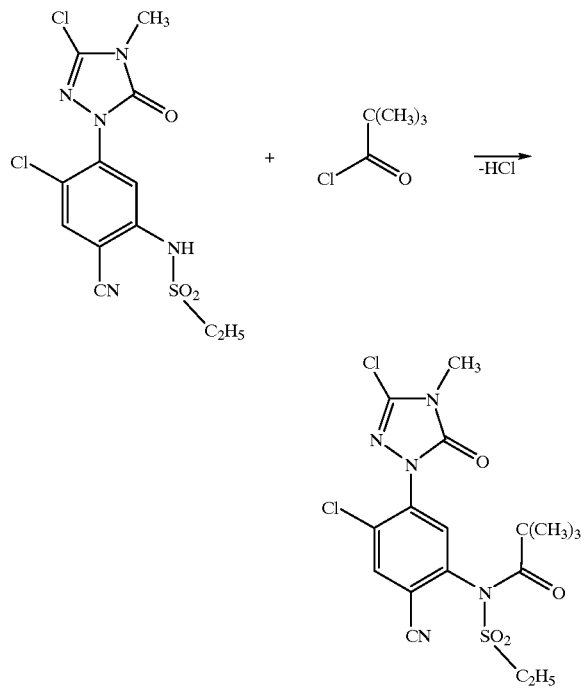

Formula (II) provides a general definition of the phenyltriazolin(ethi)ones to be used as starting materials in the process according to the invention for the preparation of compounds of the formula (I). In formula (II), $Q^1$, $R^1$ $R^2$, $R^3$ and $R^5$ preferably, or in particular, have those meanings which have already been mentioned above in connection with the description of the compounds of the formula (I) according to the invention as preferred, or particularly preferred, for $Q^1$, $R^1$ $R^2$, $R^3$ and $R^5$.

The starting materials of the formula (II) are known and/or can be prepared by known processes (cf. EP 609734/ U.S. Pat. No. 5,464,810).

Formula (III) provides a general definition of the halogeno(thio)carbonyl compounds furthermore to be used as starting materials in the process according to the invention for the preparation of compounds of the formula (I). In formula (III), $Q^2$ and $R^4$ preferably or in particular have those meanings which have already been mentioned above in connection with the description of the compounds of the formula (I) according to the invention as being preferred, or particularly preferred, for $Q^2$ and $R^4$; X preferably represents fluorine, chlorine or bromine, in particular chlorine.

The starting materials of formula (III) are known chemicals for organic synthesis.

Suitable reactants for carrying out the process according to the invention are, in general, the customary inorganic or organic bases or acid acceptors. These preferably include the acetates, amides, carbonates, hydrogen carbonates, hydrides, hydroxides or alkoxides of alkali metals or alkaline earth metals such as, for example, sodium acetate, potassium acetate or calcium acetate, lithium amide, sodium amide, potassium amide or calcium amide, sodium carbonate, potassium carbonate or calcium carbonate, sodium hydrogen carbonate, potassium hydrogen carbonate or calcium hydrogen carbonate, lithium hydride, sodium hydride, potassium hydride or calcium hydride, lithium hydroxide, sodium hydroxide, potassium hydroxide or calcium hydroxide, sodium methoxide, sodium ethoxide, sodium n- or i-propoxide, sodium n-, i-, s- or t-butoxide, potassium methoxide, potassium ethoxide, potassium n- or i-propoxide or potassium n-, i-, s- or t-butoxide, furthermore also basic organic nitrogen compounds such as, for example, trimethylamine, triethylamine, tripropylamine, tributylamine, ethyl-diisopropylamine, N,N-dimethylcyclohexylamine, dicyclohexylamine, ethyl-dicyclohexylamine, N,N-dimethylaniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo-[2.2.2]-octane (DABCO), 1,5-diazabicyclo[4.3.0]-non-5-ene (DBN), or 1,8-diazabicyclo[5.4.0]-undec-7-ene (DBU).

Suitable diluents for carrying out the process according to the invention are primarily inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride, ethers such as diethyl ether, diisopropyl ether, dioxane, tetrahydrofuran, ethylene glycol dimethyl ether or ethylene glycol diethyl ether; ketones such as acetone, butanone or methyl isobutyl ketone; nitriles such as acetonitrile, prmpionitrile, butyronitrile; amides such as N,N-dimethylformamide, N,N-dimethylacetamide, N-methyl-formanilide, N-methyl-pyrrolidone or hexamethylphosphoric triamide; esters such as methyl acetate or ethyl acetate, and sulphoxides such as dimethyl sulphoxide.

When carrying out the process according to the invention, the reaction temperatures can be varied within a substantial range. In general, the process is carried out at temperatures between 0° C. and 100° C., preferably between 10° C. and 80° C.

The process according to the invention is generally carried out under atmospheric pressure. However, the process according to the invention may also be carried out at elevated or reduced pressure—in general between 0.1 bar and 10 bar.

To carry out the process according to the invention, the starting materials are generally employed in approximately equimolar amounts. However, it is also possible to use one of the components in a larger excess. In general, the reaction is carried out in a suitable diluent in the presence of a reaction auxiliary, and the reaction mixture is generally stirred for several hours at the temperature required. Working-up is carried out by customary methods (cf. the Preparation Examples).

The active compounds according to the invention can be used as defoliants, desiccants, haulm killers and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Tuifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echiinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria., Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial crops, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pastures, and for the selective control of weeds in annual cultures.

The compounds of the formula (I) according to the invention are particularly suitable for the selective control of dicotyledonous weeds in monocotyledonous and dicotyledonous crops, both pre- and post-emergence.

The active compounds can be converted into the customary formulations, such as solutions, emulsions, wettable powders, suspensions, powders, dusts, pastes, soluble powders, granules, suspension emulsion concentrates, natural and synthetic materials impregnated with active compound, and microencapsulations in polymeric substances.

These formulations are produced in a known manner, for example by mixing the active compounds with extenders, that is, liquid solvents and/or solid carriers, optionally with the use of surface-active agents, that is, emulsifier agents and/or dispersants and/or foam-formers.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, c:hloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; as emulsifiers and/or foam-formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; as dispersants there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, ready mixes or tank mixes being possible.

Examples of known herbicides which are suitable for the mixtures are acetochlor, acifluorofen(-sodium), aclonilfen, alachlor, alloxydim(-sodium), ametryne, amidochlor, amidosulphuron, asulam, atrazine, azimsulphuron, benazolin, benfuresate, bensulphuron(-methyl), bentazone, benzofenap, benzoylprop(-ethyl), bialaphos, bifenox, bromobutide, bromofenoxime, bromoxynil, butachlor, butylate, cafenstrole, carbetamide, chlomethoxyfen, chloroamben, chloroidazone, chloroimuron(-ethyl), chloronitrofen, chlorosulphuron, chlorotoluron, cinmethylin, cinosulphuron, clethodim, clodinafop(-propargyl), clomazone, clopyralid, clopyrasulphuron, cloransulam(-methyl), cumyluron, cyanazine, cycloate, cyclosulphamuron, cycloxydim, cyhalofop(-butyl), 2,4-D, 2,4-DB, 2,4-DP, desmedipham, di-allate, dicamba, diclofop (-methyl), difenzoquat, diflufenican, dimefuron, dimepiperate, dimethachlor, dimetharnetryn, dimethenamide, dinitramine, diphenamnide, diquat, dithiopyr, diuron, dymron, EPTC, esprocarb, ethalfluralin, ethametsulphuron(-methyl), ethofumesate, ethexyfen, etobenzanide, fenoxaprop(-ethyl), flamprop(-isopropyl), flamprop(-isopropyl-L), flamprop(-methyl), flazasulphuron, fluazifop(-butyl), flumetsulam, flumiclorac(-pentyl), fluioxazine, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate(-ammonium), glyphosate(-isopropylaurnonium), halosafen, haloxyfop(-ethoxyethyl), hexazinone, imazamethabenz(-methyl), imazamethapyr, imazamox, imazapyr, imazaquin, imazethapyr, imazc, sulphuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulphuron(-methyl), molinate, monolinuron, naproanilide, napropamide, neburon, nicosulphuron, norflurazon, orbencarb, oryzalin, oxadiazon, oxyfluorofen, paraquat, pendimethcalin, phenmedipham, piperophos, pretilachlor, primisulphuron(-methyl), prometryn, propachlor, propanil, propaquizafop, propyzarnide, prosulphocarb, prosulphuron, pyrazolate, pyrazosulphuron (-ethyl), pyrazoxyfen, pyributicarb, pyridate, pyrithiobac(-sodium), quinchlorac, quinmerac, quizalofop(-ethyl), quizalofop(-p-tefuryl), rimsulphuron, sethoxydim, simazine, simetryn, sulcotrione, sulphentrazone, sulphometuron(-methyl), sulphosate, tebutam, tebuthiuron, terbuthylazine, terbutryn, thenylchlor, thiafluamide, thiazopyr, thidiazimin, thifensulphuron(-methyl), thiobencarb, tiocarbazil, tralkoxydim, tri-allate., triasulphuron, tribenuron(-methyl), triclopyr, tridiphane, trifluralin and triflusulphuron.

A mixture with other known active compounds such as fungicides, insecticides, acaricides, nematicides, bird repellents, plant nutrients and soil conditioners is also possible.

The active compounds may be applied as such, in the form of their formulations or of the use forms prepared therefrom by further dillution, such as ready-to-use solutions, suspensions, emulsions, powders, pastes and granules. They are applied in the customary manner, for example by pouring, spraying, atomizing, spreading.

The active compounds according to the invention can be applied before or after plant emergence. They may also be incorporated into the soil prior to planting.

The amount of active compound applied can vary within a substantial range. It depends essentially on the nature of the desired effect. In general, the application rates are between 1 g and 10 kg of active compound per hectare of soil surface, preferably between 5 g and 5 kg per ha.

Preparation and use of the active compounds according to the invention can be seen from the examples which follow.

PREPARATION EXAMPLES

Example 1

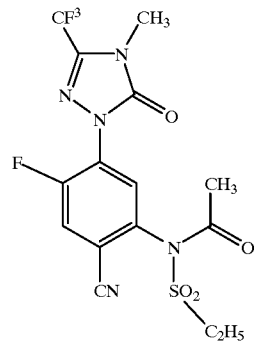

A solution of 0.4 g (5 mmol) of acetyl chloride in 20 ml of acetonitrile is added dropwise at room temperature (approx. 20° C.) to a stirred mixture of 2.0 g of 2-(4-cyano-5-ethylsulphonylamino-2-fluoro-phenyl)-4-methyl-5-trifluoromethyl-2,4-dihydro-3H-1,2,4-triazol-3-one, 0.50 g of (5 mmol) triethylamine and 40 ml of acetonitrile, and the reaction mixture is stirred for 4 hours at room temperature. A further 0.2 g of acetyl chloride and a further 0.25 g of triethylamine are then added, and stirring is continued for 15 hours at room temperature. After the mixture has been diluted with ice-water to approximately twice its volume, it is acidified with 2N hydrochloric acid and then shaken with methylene chloride. The organic phase is separated off, dried over sodium sulphate and filtered. The filtrate is concentrated in a water pump vacuum, the residue is stirred with water and the crystalline product thus obtained is isolated by filtration with suction.

This gives 1.8 g (82% of theory) of 2-[5-(N-acetyl-N-ethylsulphonylamino)-4-cyano-2-fluoro-phenyl]-4-methyl-5-trifluoromethyl-2,4-dihydro-3H-1,2,4-triazol-3-one of melting point 179° C.

Other compounds of the formula (I) which can be prepared analogously to Example 1 following the general description of the preparation process according to the tion are, for example, those in Table 1 which follows.

TABLE 1

Examples of the compounds of the formula (I)

| Ex. No. | $Q^1$ | $Q^2$ | $R^1$ | $R^2$ | $R^3$ | $R^4$ | $R^5$ | Melting point (° C.) |
|---|---|---|---|---|---|---|---|---|
| 2 | O | O | $CF_3$ | $CH_3$ | F | phenyl | $C_2H_5$ | 147 |
| 3 | O | O | $CF_3$ | $CH_3$ | F | 3-methylphenyl | $C_2H_5$ | 137 |
| 4 | O | O | $CF_3$ | $CH_3$ | F | 3-chlorophenyl | $C_2H_5$ | 158 |
| 5 | O | O | $CF_3$ | $CH_3$ | F | 2,4-dichlorophenyl | $C_2H_5$ | 160 |
| 6 | O | O | $CF_3$ | $CH_3$ | F | benzyl (-CH$_2$-phenyl) | $C_2H_5$ | 212 |
| 7 | O | O | $CF_3$ | $CH_3$ | F | 4-chlorophenyl | $C_2H_5$ | 179 |

TABLE 1-continued
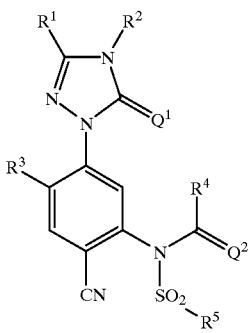
Examples of the compounds of the formula (I)
| Ex. No. | $Q^1$ | $Q^2$ | $R^1$ | $R^2$ | $R^3$ | $R^4$ | $R^5$ | Melting point (° C.) |
|---|---|---|---|---|---|---|---|---|
| 8 | O | O | $CF_3$ | $CH_3$ | F | 4-CH₃-C₆H₄ | $C_2H_5$ | 179 |
| 9 | O | O | $CF_3$ | $CH_3$ | F | cyclopropyl | $C_2H_5$ | 153 |
| 10 | O | O | $CF_3$ | $CH_3$ | F | $C_2H_5$ | $C_2H_5$ | 151 |
| 11 | O | O | $CF_3$ | $CH_3$ | F | 2-CH₃-C₆H₄ | $C_2H_5$ | 111 |
| 12 | O | O | $CF_3$ | $CH_3$ | F | C₆H₅-O-CH₂CH₂- | $C_2H_5$ | 123 |
| 13 | O | O | $CF_3$ | $CH_3$ | F | C₆H₅-CH₂CH₂- | $C_2H_5$ | 101 |
| 14 | O | O | $CF_3$ | $CH_3$ | F | 2-furyl | $C_2H_5$ | 166 |
| 15 | O | O | $CF_3$ | $CH_3$ | F | $CH_2Cl$ | $C_2H_5$ | 158 |

TABLE 1-continued
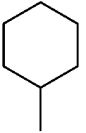
(I)
Examples of the compounds of the formula (I)
| Ex. No. | $Q^1$ | $Q^2$ | $R^1$ | $R^2$ | $R^3$ | $R^4$ | $R^5$ | Melting point (° C.) |
|---|---|---|---|---|---|---|---|---|
| 16 | O | O | $CF_3$ | $CH_3$ | F | 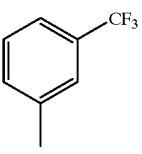 | $C_2H_5$ | 79 |
| 17 | O | O | $CF_3$ | $CH_3$ | F | 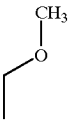 | $C_2H_5$ | 158 |
| 18 | O | O | $CF_3$ | $CH_3$ | F | 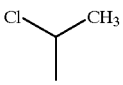 | $C_2H_5$ | 121 |
| 19 | O | O | $CF_3$ | $CH_3$ | F | 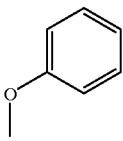 | $C_2H_5$ | 144 |
| 20 | O | O | $CF_3$ | $CH_3$ | F | —CH=$CH_2$ | $C_2H_5$ | 180 |
| 21 | O | O | $CF_3$ | $CH_3$ | F | 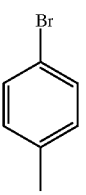 | $C_2H_5$ | 144 |
| 22 | O | O | $CF_3$ | $CH_3$ | F | $C_4H_9$-n | $C_2H_5$ | 139 |
| 23 | O | O | $CF_3$ | $CH_3$ | F |  | $C_2H_5$ | 189 |

TABLE 1-continued
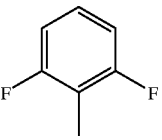
(I)
Examples of the compounds of the formula (I)
| Ex. No. | Q¹ | Q² | R¹ | R² | R³ | R⁴ | R⁵ | Melting point (° C.) |
|---|---|---|---|---|---|---|---|---|
| 24 | O | O | CF₃ | CH₃ | F | 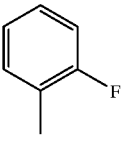 | C₂H₅ | 161 |
| 25 | O | O | CF₃ | CH₃ | F | 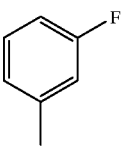 | C₂H₅ | 124 |
| 26 | O | O | CF₃ | CH₃ | F | 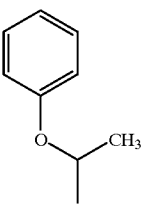 | C₂H₅ | 142 |
| 27 | O | O | CF₃ | CH₃ | F | 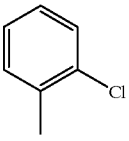 | C₂H₅ | 137 |
| 28 | O | O | CF₃ | CH₃ | F | 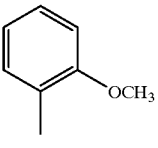 | C₂H₅ | 177 |
| 29 | O | O | CF₃ | CH₃ | F |  | C₂H₅ | 162 |

TABLE 1-continued

Examples of the compounds of the formula (I)

(I)

| Ex. No. | Q¹ | Q² | R¹ | R² | R³ | R⁴ | R⁵ | Melting point (° C.) |
|---|---|---|---|---|---|---|---|---|
| 30 | O | O | CF$_3$ | CH$_3$ | F | 4-methoxyphenyl (OCH$_3$) | C$_2$H$_5$ | 141 |
| 31 | O | O | CF$_3$ | CH$_3$ | F | 2,3,6-trifluoro-phenyl | C$_2$H$_5$ | 176 |
| 32 | O | O | CF$_3$ | CH$_3$ | F | CH(OC$_2$H$_5$)$_2$ | C$_2$H$_5$ | 149 |
| 33 | O | O | CF$_3$ | CH$_3$ | F | 4-tert-butylphenyl (C(CH$_3$)$_3$) | C$_2$H$_5$ | 191 |
| 34 | O | O | CF$_3$ | CH$_3$ | F | CH=CH-OC$_2$H$_5$ (propenyl) | C$_2$H$_5$ | 168 |
| 35 | O | O | CF$_3$ | CH$_3$ | F | CH$_2$C(CH$_3$)$_3$ | C$_2$H$_5$ | 170 |
| 36 | O | O | CF$_3$ | CH$_3$ | F | CH(CH$_3$)$_2$ | C$_2$H$_5$ | 141 |
| 37 | O | O | CF$_3$ | CH$_3$ | F | C$_4$H$_9$-i | C$_2$H$_5$ | 168 |
| 38 | O | O | CF$_3$ | CH$_3$ | F | OC$_2$H$_5$ | C$_2$H$_5$ | (amorphous) |

TABLE 1-continued

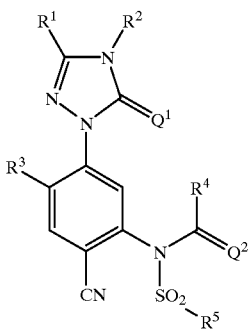

Examples of the compounds of the formula (I)

| Ex. No. | Q¹ | Q² | R¹ | R² | R³ | R⁴ | R⁵ | Melting point (° C.) |
|---|---|---|---|---|---|---|---|---|
| 39 | O | O | CF₃ | CH₃ | F | 3,4-dimethylisoxazol-5-yl | C₂H₅ | 197 |
| 40 | O | O | CF₃ | CH₃ | F | 5-methoxy-3-methylisoxazol-... | C₂H₅ | 167 |
| 41 | O | O | CF₃ | CH₃ | F | C(CH₃)₃ | C₂H₅ | (amorphous) |
| 42 | O | O | CF₃ | CH₃ | F | thien-2-yl | C₂H₅ | 100 |
| 43 | O | O | CF₃ | CH₃ | F | C₃H₇-n | C₂H₅ | 169 |

USE EXAMPLES

Example A

Pre-emergence test

Solvent: 5 parts by weight of acetone Emulsifier: 1 part by weight of alkylaryl polyglycol ether To prepare a suitable preparation of active compound, 1 part by weight of active compound is mixed with the stated amount of solvent, the stated amount of emulsifier is added, and the concentrate is diluted with water to the desired concentration.

Seeds of the test plants are sown in normal soil. After approx. 24 hours, the soil is sprayed with the active compound preparation in such a way that the quantities of active compound desired in each case are applied per unit area. The concentration of the spray mixture is chosen such that the quantities of active compound desired in each case are applied in 1000 l of water/ha.

After three weeks, the extent of damage to the plants is scored in % damage in comparison with the development of the untreated control.

The figures denote:

0%=no action (like untreated control)

100%=total destruction

In this test, a very potent action against weeds such as Abutilon (100%), Amaranthus (100%), Chenopodium (100%), Datura (100%), Alopecurus (100%), Galium (100%). Matricaria (100%), Stellaria (100%) and Veronica (90 to 100%) is shown, for example, by the compounds of Preparation Example 2, 3 and 8 at application rates of between 15 g and 60 g/ha, combined with good tolerance by crop plants such as, for example, maize, soya and wheat (in each case 0%).

Example B

Post-emergence test

Solvent: 5 parts by weight of acetone Emulsifier: 1 part by weight of alkylaryl polyglycol ether To prepare a suitable preparation of active compound, 1 part by weight of active compound is mixed with the stated amount of solvent, the stated amount of emulsifier is added, and the concentrate is diluted with water to the desired concentration.

Test plants which have a height of 5–15 cm are sprayed with the active compound preparation in such a way that the quantities of active compound desired in each case are applied per unit area. The concentration of the spray mixture is chosen such that the quantities of active compound desired in each case are applied in 1000 l of water/ha.

After three weeks, the extent of damage to the plants is scored in % damage in comparison with the development of the untreated control.

The figures denote:

0%=no action (like untreated control)

100%=total destruction

In this test, a very potent action against weeds such as Amaranthus (100%), Chenopodium (100%), Galium (98 to 100%), Lamium (100%), Stellaria (100%) and Veronica (98 to 100%) is shown, for example, by the compounds of Preparation Example 2, 3 and 8 at application rates of between 15 g and 60 g/ha, combined with good tolerance by crop plants such as, for example, barley and wheat (in each case 0%).

What is claimed is:

1. A phenyltriazolin(ethi)one of formula (I),

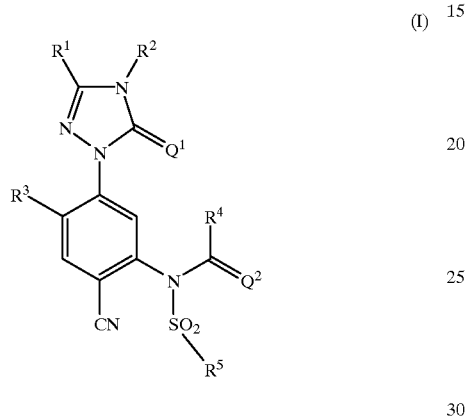

in which $Q^1$ and $Q^2$ are identical or different and represent O or S, $R^1$ represents hydrogen, cyano, halogen or one of the radicals —$R^6$, —O—$R^6$, —$SR^6$, —SO—$R^6$ or —$SO_2$—$R^6$, $R^2$ represents hydrogen, hydroxyl, amino or one of the radicals —$R^6$, —O—$R^6$ or —N=$CR^6R^7$, $R^3$ represents hydrogen, halogen, alkyl having 1 to 4 carbon atoms or halogenoalkyl having 1 to 4 carbon atoms and 1 to 3 identical or different halogen atoms, $R^4$ represents hydrogen, alkoxycarbonyl having 1 to 6 carbon atoms in the alkoxy group or one of the radicals —$R^6$, —O—$R^6$, —$SR^6$, —NH—$R^6$ or —$NR^6R^7$, $R^5$ represents amino, hydroxyl or one of the radicals —$R^6$ or —$NR^6R^7$, $R^6$ represents unsubstituted, monosubstituted or polysubstituted alkyl having 1 to 10 carbon atoms, wherein the substituents are identical or different and are selected from the group consisting of halogen, cyano, carboxyl, carbamoyl, thiocarbamoyl, alkoxy having from 1 to 6 carbon atoms, alkoxyalkoxy having from 1 to 6 carbon atoms in each moiety, alkylthio having from 1 to 6 carbon atoms in the alkyl moiety, alkylsulphinyl having from 1 to 6 carbon atoms in the alkyl moiety, alkylsulphonyl having from 1 to 6 carbon atoms in the alkyl moiety, alkylcarbonyl having from 1 to 6 carbon atoms in the alkyl moiety, N-alkyl-aminocarbonyl having from 1 to 6 carbon atoms in the alkyl moiety, N,N-dialkyl-aminocarbonyl having from 1 to 6 carbon atoms in each alkyl moiety, trialkylsilyl having from 1 to 6 carbon atoms in the alkyl moiety, and alkylsulphonylaminocarbonyl having from 1 to 6 carbon atoms in the alkyl moiety;

or represents unsubstituted, monohalogen-substituted or polyhalogen-substituted alkenyl having 2 to 8 carbon atoms;

or represents unsubstituted, monohalogen-substituted or polyhalogen-substituted alkinyl having 2 to 8 carbon atoms;

or represents unsubstituted, monosubstituted or polysubstituted cycloalkyl having 3 to 7 carbon atoms, wherein the substituents are identical or different and are selected from the group consisting of halogen and alkyl having from 1 to 4 carbon atom;

or represents unsubstituted, monosubstituted or polysubstituted aryl having 6 to 10 carbon atoms, and unsubstituted, monosubstituted or polysubstituted arylalkyl, aryloxyalkyl and arylalkoxyalkyl each of which have 6 to 10 carbon atoms in the aryl group and 1 to 4 carbons in the alkyl group, wherein the substituents in the aryl group are identical or different and are selected from the group consisting of halogen, cyano, nitro, amino, N-acetylamino, alkyl having 1 to 6 carbon atoms, alkoxy having 1 to 6 carbon atoms, alkylthio having 1 to 6 carbon atoms, alkylsulphinyl having 1 to 6 carbon atoms, alkylsulphonyl having 1 to 6 carbon atoms, halogenoalkyl having 1 to 6 carbon atoms and 1 to 3 identical or different halogen atoms, halogenoalkoxy having 1 to 6 carbon atoms and 1 to 3 identical or different halogen atoms, halogenoalkylthio having 1 to 6 carbon atoms and 1 to 3 identical or different halogen atoms, halogeno-alkylsulphinyl having 1 to 6 carbon atoms and 1 to 3 identical or different halogen atoms, halogenoalkylsulphonyl having 1 to 6 carbon atoms and 1 to 3 identical or different halogen atoms, alkoxycarbonyl having 1 to 6 carbon atoms in the alkyl moiety, alkoximinoalkyl having 1 to 6 carbon atoms in the alkyl moiety, unsubstituted, monosubstituted or polysubstituted phenyls wherein the substituents are selected from the group consisting of halogen, alkyl having 1 to 6 carbon atoms, alkoxy having 1 to 6 carbon atoms, halogenoalkyl having from 1 to 6 carbon atoms and 1 to 3 identical or different halogen atoms, and halogenoalkoxy having from 1 to 6 carbon atoms and 1 to 3 identical or different halogen atoms; and $R^7$ represents hydrogen or unsubstituted, monosubstituted or polysubstituted alkyl having from 1 to 8 carbon atoms, wherein the substituents are identical or different and are selected from the group consisting of halogen, cyano, carboxyl, carbamoyl, thiocarbamoyl, alkoxy having 1 to 8 carbon atoms, alkoxyalkoxy having 1 to 8 carbon atoms in each moiety, alkylthio having 1 to 8 carbon atoms, alkylsulphinyl having 1 to 8 carbon atoms, alkylsulphonyl having 1 to 8 carbon atoms, alkoxycarbonyl having 1 to 8 carbon atoms in the alkyl moiety, N-alkylaminocarbonyl having 1 to 8 carbon atoms in the alkyl moiety, N,N-dialkylaminocarbonyl having 1 to 8 carbon atoms in each alkyl moiety, trialkylsilyl having 1 to 8 carbon atoms in each alkyl moiety, and alkylsulphonylaminocarbonyl having 1 to 8 carbon atoms in the alkyl moiety;

or represents unsubstituted, monohalogen-substituted, or polyhalogen-substituted alkenyl and alkinyl each having from 2 to 8 carbon atoms;

or represents unsubstituted, monosubstituted or polysubstituted cycloalkyl having from 3 to 7 carbon atoms, wherein the substituents are identical or different and are selected from the group consisting of halogen and alkyl having 1 to 4 carbon atoms.

2. A herbicidal composition comprising an effective amount of a phenyltriazolin(ethi)one of the formula (I) according to claim 1 and a liquid solvent and/or solid carrier and/or surface-active substance.

3. A method of controlling undesired plants, comprising applying a herbicidally effective amount of a phenyltriazolin (ethi)one of the formula (I) according to claim 1 to undesired plants and/or their environment.

4. The phenyltriazolin(ethi)one of

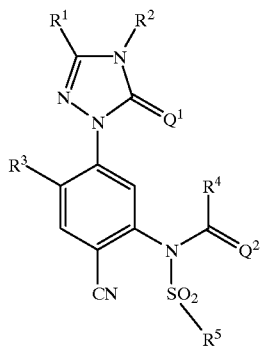

(I)

wherein $Q^1$ and $Q^2$ represent O, $R^1$ represents $CF_3$, $R^2$ represents $CH_3$, $R^3$ represents F, $R^4$ represents $-CH=CH_2$, and $R^5$ represents $C_2H_5$.

5. A phenyltriazolin(ethi)one according to claim 1, wherein $Q^1$ and $Q^2$ are identical or different and represent O or S, $R^1$ represents hydrogen, fluorine, chlorine, bromine or one of the radicals $-R^6$, $-O-R^6$, $-SR^6$, $-SO-R^6$ or $-SO_2-R^6$, $R^2$ represents hydrogen, hydroxyl, amino or one of the radicals $-R^6$, $-O-R^6$ or $-N=CR^6R^7$, $R^3$ represents hydrogen, fluorine, chlorine, bromine, or represents straight-chain or branched alkyl having 1 to 3 carbon atoms or straight-chain or branched halogenoalkyl having 1 to 3 carbon atoms and 1 to 3 identical or different halogen atoms, $R^4$ represents hydrogen, or represents alkoxycarbonyl having 1 to 4 carbon atoms in the alkoxy group, or one of the radicals $-R^6$, $-O-R^6$, $-S-R^6$, $-NH-R^6$ or $-NR^6R^7$, $R^5$ represents amino, hydroxyl or one of the radicals $-R^6$ or $-NR^6R^7$, $R^6$ represents straight-chain or branched alkyl having 1 to 6 carbon atoms which is unsubstituted or monosubstituted with a substituent selected from cyano, carboxyl, carbamoyl, thiocarbamoyl, in each case straight-chain or branched alkoxy, alkoxyalkoxy, alkylthio, alkylsulphinyl, alkylsulphonyl, alkoxycarbonyl, N-alkyl-aminocarbonyl, N,N-dialkyl-aminocarbonyl, trialkylsilyl or alkylsulphonylaminocarbonyl, each of which has 1 to 4 carbon atoms in the individual alkyl moieties;

or represents straight-chain or branched halogenoalkyl having 1 to 4 carbon atoms and 1 to 3 identical or different halogen;

or represents alkenyl or alkinyl, each of which has 2 to 6 carbon atoms and each of which is unsubstituted or monosubstituted to trisubstituted by identical or different halogen;

or represents cycloalkyl having 3 to 6 carbon atoms which is unsubstituted or monosubstituted to trisubstituted by identical or different substituents selected from halogen and straight-chain or branched alkyl having 1 to 3 carbon atoms;

or represents phenyl, phenylalkyl or phenoxyalkyl, wherein the phenylalkyl and phenoxy alkyl each have 1 to 3 carbon atoms in the straight-chain or branched alkyl moiety, and each of phenyl, phenylalkyl or phenoxyalkyl is unsubstituted or is monosubstituted to trisubstituted in the phenyl moiety by identical or different substituents, the substituents being selected from fluorine, chlorine, bromine, cyano, nitro, amino, N-acetyl-amino, in each case straight-chain or branched alkyl, alkoxy, alkylthio, alkylsulphinyl or alkylsulphonyl, each of which has 1 to 4 carbon atoms, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 3 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents from amongst halogen and/or straight-chain or branched alkyl or alkoxy, each of which has 1 to 4 carbon atoms, and/or straight-chain or branched halogenoalkyl or halogenoalkoxy, each of which has 1 to 4 carbon atoms and 1 to 3 identical or different halogen atoms; and $R^7$ represents hydrogen or straight-chain or branched alkyl having 1 to 4 carbon atoms which is unsubstituted or monosubstituted with a substituent selected from cyano, carboxyl, carbamoyl, in each case straight-chain or branched alkoxy, alkoxyalkoxy, alkylthio, alkylsulphinyl, alkylsulphonyl, alkoxycarbonyl, N-alkyl-aminocarbonyl, N,N-dialkyl-aminocarbonyl, trialkylsilyl or alkylsulphonylaminocarbonyl, each of which has 1 to 4 carbon atoms in the individual alkyl moieties;

or represents straight-chain or branched halogenoalkyl having 1 to 4 carbon atoms and 1 to 3 identical or different halogen atoms;

or represents alkenyl or alkinyl, each of which, has 2 to 4 carbon atoms and each of which is unsubstituted or is monosubstituted to trisubstituted by identical or different halogen atoms;

or represents cycloalkyl having 3 to 6 carbon atoms which is unsubstituted or is monosubstituted to trisubstituted by identical or different substituents from halogen and straight-chain and branched alkyl having 1 to 3 carbon atoms.

6. A phenyltriazolin(ethi)one according to claim 1, wherein $Q^1$ and $Q^2$ are each O;

$R^1$ represents hydrogen, chlorine, bromine or one of the radicals $-R^6$, $-O-R^6$, $-S-R^6$, $-SO-R^6$ or $-SO_2-R^6$;

$R^2$ represents hydrogen or one of the radicals $-R^6$ or $-O-R^6$;

$R^3$ represents hydrogen, fluorine or chlorine;

$R^4$ represents hydrogen or one of the radicals —$R^6$, O—$R^6$, —S—$R^6$, —NH—$R^6$ or —$NR^6R^7$;

$R^5$ represents one of the radicals —$R^6$ or —$NR^6R^7$;

$R^6$ represents methyl, ethyl, n- or i-propyl, n-, i-, s- or t-butyl, each of which is unsubstituted or is monosubstituted or disubstituted with substituents selected from cyano, carboxyl, carbamoyl, and straight-chain and branched alkoxy, alkoxyalkoxy, alkylthio, alkylsulphinyl, alkylsulphonyl, alkoxycarbonyl, N-alkyl aminocarbonyl, N,N-dialkyl-aminocarbonyl, trialkylsilyl and alkylsulphonylaminocarbonyl, each of which has 1 to 4 carbon atoms in the individual alkyl moieties;

or represents halogenoalkyl having 1 or 2 carbon atoms and 1 to 3 identical or different halogen atoms;

or represents alkenyl or alkinyl, each of which has 2 to 5 carbon atoms and each of which is unsubstituted or is monosubstituted or disubstituted by halogen;

or represents cyclopropyl, cyclopentyl or cyclohexyl, each of which is unsubstituted or is monosubstituted or disubstituted by identical or different substituents selected from fluorine, chlorine, methyl and ethyl;

or represents phenyl or benzyl, each of which is unsubstituted or is monosubstituted, disubstituted or trisubstituted by identical or different substituents selected from fluorine, chlorine, bromine, cyano, nitro, amino, N-acetyl-amino, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, methylsulphonyl, trifluoromethyl, difluoromethyl, trifluoromethoxy, difluoromethoxy, trifluoromethylthio, trifluoromethylsulphinyl, trifluoromethylsulphonyl, methoxycarbonyl, ethoxycarbonyl, methoximinomethyl, methoximinoethyl, ethoximinomethyl, ethoximinoethy; and $R^7$ represents hydrogen, or represents methyl, ethyl, n- or i-propyl, n- or i-butyl, each of which is unsubstituted or is monosubstituted with a substituent selected from cyano, carboxyl, carbamoyl, in each case straight-chain or branched alkoxy, alkoxyalkoxy, alkylthio, alkylsulphinyl, alkylsulphonyl, alkoxycarbonyl, N-alkyl-aminocarbonyl, N,N-dialkyl-aminocarbonyl, each of which has 1 to 4 carbon atoms in the alkyl groups;

or represents halogenoalkyl having 1 or 2 carbon atoms and 1 to 3 identical or different halogen atoms;

or represents alkenyl or alkinyl, each of which has 2 to 5 carbon atoms and each of which is unsubstituted or is monosubstituted or disubstituted by halogen;

or represents cyclopropyl, cyclopentyl or cyclohexyl, each of which is unsubstituted or monosubstituted or disubstituted by identical or different substituents selected from fluorine, chlorine, methyl and lethyl.

* * * * *